(12) United States Patent
Nilsson et al.

(10) Patent No.: US 12,102,507 B2
(45) Date of Patent: Oct. 1, 2024

(54) EAR CUSHION SYSTEM WITH FLUID FLOW, EAR CUSHION, FLUID GUIDE DEVICE, HEADSET AND HEADGEAR WITH SUCH SYSTEM

(71) Applicant: 3M INNOVATIVE PROPERTIES COMPANY, St. Paul, MN (US)

(72) Inventors: Jonas A. Nilsson, Värnamo (SE); Van Cuong Bui, Värnamo (SE); Patrick R. T. Hjort, Värnamo (SE)

(73) Assignee: 3M Innovative Properties Company, St. Paul, MN (US)

( * ) Notice: Subject to any disclaimer, the term of this patent is extended or adjusted under 35 U.S.C. 154(b) by 112 days.

(21) Appl. No.: 17/756,450

(22) PCT Filed: Nov. 24, 2020

(86) PCT No.: PCT/IB2020/061086
§ 371 (c)(1),
(2) Date: May 25, 2022

(87) PCT Pub. No.: WO2021/105874
PCT Pub. Date: Jun. 3, 2021

(65) Prior Publication Data
US 2023/0000685 A1 Jan. 5, 2023

(30) Foreign Application Priority Data

Nov. 27, 2019 (EP) ..................................... 19211896

(51) Int. Cl.
*A61F 11/14* (2006.01)
*H04R 1/10* (2006.01)
*A61F 7/00* (2006.01)

(52) U.S. Cl.
CPC ................ *A61F 11/14* (2013.01); *H04R 1/10* (2013.01); *A61F 2007/0005* (2013.01)

(58) Field of Classification Search
None
See application file for complete search history.

(56) References Cited

U.S. PATENT DOCUMENTS

| 2,901,751 | A | | 9/1959 | Gales et al. |
| 4,700,410 | A | * | 10/1987 | Westgate ............... A42B 3/166 |
| | | | | 2/209 |
| 9,344,781 | B2 | * | 5/2016 | Hamilton ............... G10L 13/00 |

(Continued)

FOREIGN PATENT DOCUMENTS

| CN | 204319547 U | 5/2015 |
| WO | 2018139995 A1 | 8/2018 |
| WO | 2019104172 A1 | 5/2019 |

OTHER PUBLICATIONS

International Search Report for PCT International Application No. PCT/IB2020/061086, mailed on Jan. 19, 2021, 5 pages.

*Primary Examiner* — Paul W Huber
(74) *Attorney, Agent, or Firm* — Katherine M. Scholz; Steven A. Bern

(57) ABSTRACT

The present disclosure relates to a system 10 comprising an ear cushion 20 for a headset 100, a fluid supply 30 and a fluid guide device 40 connected to the ear cushion 20. The present disclosure further relates to an ear cushion 20 for a headset 100, a fluid guide device 40 for a headset 100. Moreover, the present disclosure relates to a headset 100 as well as to a headgear 200 comprising such a system 10.

17 Claims, 5 Drawing Sheets

(56) References Cited

U.S. PATENT DOCUMENTS

| | | | |
|---|---|---|---|
| 9,621,979 B2* | 4/2017 | Bakalos | H04R 1/1041 |
| 9,942,647 B2* | 4/2018 | Di Censo | H04R 1/1091 |
| 10,536,763 B2* | 1/2020 | Slater | H04R 1/1041 |
| 11,228,829 B2* | 1/2022 | Hanes | H04R 1/1091 |
| 2012/0063619 A1* | 3/2012 | Hildebrandt | H04R 3/04 |
| | | | 381/74 |
| 2012/0102629 A1 | 5/2012 | Lott et al. | |
| 2015/0139458 A1* | 5/2015 | Ruwe | H04R 1/1091 |
| | | | 381/384 |
| 2015/0312670 A1 | 10/2015 | Candidus et al. | |
| 2017/0099539 A1 | 4/2017 | Di Censo | |
| 2022/0312099 A1* | 9/2022 | Dory | H04R 1/1008 |

* cited by examiner

EAR CUSHION SYSTEM WITH FLUID FLOW, EAR CUSHION, FLUID GUIDE DEVICE, HEADSET AND HEADGEAR WITH SUCH SYSTEM

CROSS REFERENCE TO RELATED APPLICATIONS

This application is a national stage filing under 35 U.S.C. 371 of PCT/IB2020/061086, filed Nov. 24, 2020, which claims the benefit of EP Application No.: 19211896.6, filed Nov. 27, 2019, the disclosure of which is incorporated by reference in its/their entirety herein.

PRESENT DISCLOSURE

The present disclosure relates to a system comprising an ear cushion for a headset, a fluid supply and a fluid guide device connected to the ear cushion. The present disclosure further relates to an ear cushion for a headset and a fluid guide device for a headset. Moreover, the present disclosure relates to a headset as well as to a headgear comprising such a system.

BACKGROUND ART

Headsets are used in very different environments. Often the users of a headset are wearing those headsets for a longer time without taking them off. Typically, headsets have two cups which cover the ears of the user or wearer and which are connected to one another by a headband. Each cup further typically is formed by a rigid shell that is furnished by a noise damping material, for example a foamed material.

There is a general desire to make headsets user-friendly, in particular to guarantee wearing compliance of headsets, especially in noisy environments for a longer time. Often a wearer sweats in an area in which the headset is in contact with the wearer's skin. There are headsets which are furnished with ear cushions made of materials that have moisture absorbent properties. Another problem is that, in a cold environment, the cups and the ear cushion could be too cold, for example, in cold storage houses.

For example, WO 2019/104172 discloses a ring-shaped cushion for a hearing protector or audio headset. The cushion has a circumferential contact pad for sealing on a wearer's head and an attachment for sealing with an ear-muff/cup. The cushion further has a sound insulation tube that inwardly defines an inner space. The sound insulation tube extends between the contact pad and the attachment. The cushion has a ventilation passage that extends entirely through the cushion between an inlet opening in the contact pad and an area outside of the inner space. The cushion may further include one or more physiological sensors to monitor the health of a wearer. However, a tempering of ear cushions by a such passive cooling system might not be sufficient enough, in particular for higher and/or lower temperatures.

There is still a need for a headset which provides increased wearing comfort in different environments.

SUMMARY OF THE PRESENT DISCLOSURE

The present disclosure relates to a system that comprises at least one ear cushion for a headset and a fluid supply for supplying a fluid for tempering the ear cushion. The ear cushion comprises a fluid guide device that is connectable to the fluid supply. The system further comprises at least one interface for connecting the fluid guide device to the ear cushion. The present disclosure is advantageous in that it provides air or other fluids for a headset, which are cold and/or. The fluid guide device enables the transport of the fluid from the fluid supply to the ear cushion. The interface enables a solid and rigid connection between the fluid supply and the fluid guide device, this allows a reliable transport of the fluid from the supply device to the fluid guide device. The system according to the present disclosure provides for an active tempering system, which has the advantage that a fluid flows through the ear cushions by an overpressure or negative pressure in an improved way. Such an active tempering system provides for affecting the volume flow of the fluid to temper the fluid. This active tempering system has the advantage that the temperature of the ear cushions can be adapted to the environment conditions, for example, by using a heated or cooled fluid in the active tempering system. With tempering an ear cushion, it is possible to increase the comfort during wearing, because the wearer has a more pleasant feeling by using the ear cushions according to the present disclosure and with that also the wearing of a headset is more pleasant. The tempered ear cushion has the advantage that feeling unwell because of too cold and/or to warm ears by using ear cushions will be reduced or avoided and thus, the risk of wearers for being sick reduced.

The term "environment" for the purpose of the present specification particularly refers to an area outside the headset and outside an area encapsulated around a wearer's ear by the headset when worn by a wearer. In a working environment at a steadily increasing tempo, the demands on protective equipment and the like have been raised. For example, it is important that the hearing protection is employed in the correct manner, such that safety is not impaired. However, improvements to safety must not be put into effect at the expense of user friendliness and/or comfort.

Wearer/user in the context of the present disclosure are a person wearing a headset. Users may be employees and may wear the headset, for example, at work. Such work environment may be at an employer's facility, e.g. a factory or the like.

In one embodiment the ear cushion comprises at least one ventilation passage being in fluid communication with the at least one interface. The ear cushion optionally comprises at least one opening. The ventilation passage enables to temper the ear cushion evenly, all parts or zones of the ear cushion achieve a uniform temperature. The effect is that uniform temperature of the ear cushion further increases the wearing comfort. A typical production method for such ear cushion is to produce two parts of the ear cushion for example by injection molding, the connection of the two parts can be realized by ultrasonic welding. An appropriate material for the ear cushion is a polymer, for example an EPDM (ethylene propylene diene monomer rubber) foam. Other manufacturing technologies and material for producing such ear cushions are available.

In another embodiment, the ventilation passage comprises at least one air deflector. The use of air deflectors allows an improved flow of the fluid inside the ear cushion. With a deflector it is possible to influence or direct the flow of the fluid in a targeted manner, for example to achieve a better fluid distribution. This influence or directing of the flow of the fluid allows to temper the ear cushion more evenly, for example, by different flow rates in particular segments of the ventilation passage in the ear cushion.

In another embodiment, the interface is removably connected to the fluid supply from the fluid guide device. This version allows an easy replacement of the parts, for example if one of the parts is defect or contaminated.

In another embodiment the interface comprises a removable connection between the fluid guide device and the ear cushion. Such a removable connection allows for an easy replacement of the parts, for example if one of the parts is defect or contaminated.

A typical production method for the fluid guide device is to tailor, for example, a hose appropriate to the necessary requirements. A production by gas-assisted injection molding to form the fluid guide device inside a specific mold is possible, too. An appropriate material for the fluid guide device is a polymer, for example a PA (Polyamide). Other manufacturing technologies and material for producing such fluid guide devices are also available.

In a further embodiment the ventilation passage comprises at least two openings with different cross sections. The different cross sections of the openings are enabling to affect the flow of the fluid inside the ear cushion through the ventilation passage. The different cross sections are useful to equalize a pressure drop in the ventilation passage.

In another embodiment the system comprises at least one interface, wherein the opening with the smaller cross section is positioned closer to the interface. The interface allows reliable and solid connection between the fluid guide device and the ear cushion. The construction with the smaller opening near by the interface allows to affect the fluid flow volume rate and the fluid flow speed inside the ear cushion and with that inside of the ventilation passage.

In another embodiment the ear cushion is made of a porous material. The use of a porous material is suitable for the ear cushion because this material enables a good thermal isolation. Different porous materials are possible to use, in particular plastic porous materials. An ear cushion made of an open pored material or open pored foam has a plurality of openings and enables an exhaustion of the fluid from the ventilation passage to the environment. It enables an even tempering of the ear cushion.

An ear cushion made of a closed pored material or closed pored foam has the feature that no medium or material from the environment can infiltrate into the structure of the ear cushion. This helps to clean the ear cushion after using. Polymers are typical materials for open pored material and closed pored material, for example a PU (Polyurethane).

In a further embodiment, the fluid supply of the system comprises a pressure change device to affect the pressure of the fluid, to allow a movement of the fluid from the fluid supply through the fluid guide device to the ear cushion or into the reverse direction. This pressure change device enables a movement of the fluid through the fluid guide device and the ventilation passage of the ear cushion. The pressure changing device may generate an overpressure to the fluid. In this case the fluid will be pressed through the fluid guide device and the ventilation passage inside the ear cushion. Alternatively, the pressure changing device may generate a low pressure to the fluid, in this case the fluid will be sucked through the ventilation passage of the ear cushion and through the fluid guide device. Changing the pressure of the fluid may increase the fluid distribution within the ear cushion compared to a flow at a constant pressure. In both cases, using an overpressure or using a low pressure, an open system may be used. This means that the fluid can flow out to the environment or will flow into the system from the environment. Alternatively, a close loop use of the fluid in the system is possible too, this means the fluid will flow by an overpressure or by a negative pressure through the fluid guide device and the ventilation passage inside the ear cushion. In this case the fluid will be circling in the system, such a close loop system has the advantage that in an environment with quite a lot of dust, dirt or other pollution the fluid inside the here disclosed system. For such a close loop system it is useful if the system comprises at least two fluid guide devices to allow an outgoing and returning of the fluid from the fluid supply and the ear cushion. A potential pressure changing device is a belt-mounted air purification device or a powered respirator. An example for such a purification device is a 3M™ Versaflo™ TR-300 commercially available from 3M Deutschland GmbH, 41453 Neuss, Germany. The pressure change device optionally comprises a fan, a pump, a compressor, a pressure vessel or any combinations thereof. All this technical equipment mentioned before affects the pressure of the fluid in the system and thus enables a flow of the fluid in the system for an even tempering of the ear cushion.

In a further embodiment, the ear cushion of the system according to the present disclosure has no openings. Thus, a close loop is formed. The connection of the fluid supply is by at least two fluid guide devices, and no fluid flows out of the ear cushions into the environment. Thus, the ear cushion is in fluid communication with the fluid supply by the fluid guide device. Such a close loop has the advantage that the fluid flow is independent of the environment, so that unwanted influences caused by ambient temperature or by pollution of the air (as fluid) are minimized or avoided.

In a further embodiment, the system comprises a tempering device for affecting the temperature of the fluid for tempering the ear cushion. In some environments with lower temperature, for example in a cold store house or working outside in cold environments, cold ears of the user may lead to user's discomfort. In such an environment it may be very pleasant to use the ear cushion if the tempering device increases the temperature of the fluid. A device for such a solution to increase the temperature of the fluid may be a heater. In an environment with a higher temperature, for example in deserts or working nearby a blast furnace in a steel plant, a reduction of the temperature may be desired. A device for such a solution to decrease the temperature may be a cooling unit. Both solutions affect the temperature of the fluid and thus, the wearing/using of the ear cushion is more pleasant for the wearer and the compliance of wearing/using is increased.

In one embodiment, the fluid for tempering the ear cushion is air. For example, air may be provided by a pipe for the use in the system according to the present disclosure. The pipe may be a part of an air supply unit. Alternatively, a pressure cylinder/bottle may be the supply unit. The supply unit is connected to a device for transporting the fluid to the supply unit, examples for device for transporting the fluid can be a tube/pipe/hose. Alternatively, the system may use ambient air or compressed air from a specific ventilation system, for example a permanently installed ventilation system in a factory hall. In this case the fluid supply sucks the ambient air directly from the environment of the system and presses the ambient air through the fluid guide device into the ear cushion. Alternatively, also a sucking of the ambient air through the ear cushion and the fluid guide device is conceivable. The use of air, ambient air, compressed air or a mixture of both as a fluid has the advantage, that the handling of these fluids are simple, because it is possible to blow out of the system into the environment without polluting the environment by using air in the system, as opposed to hazard or bad fluid. The tempering of air, ambient air, compressed air or a mixture of both, is easy and with relative economic widely used equipment realizable.

In yet another embodiment, the system according to the present disclosure comprises a filter for filtering the fluid.

This may be beneficial as impurities may be removed from the fluid. This may be of particular importance if ambient air is used as fluid.

In one embodiment, the fluid supply of the system comprises a powered respirator. This is beneficial because the fluid for tempering the ear cushions is the same fluid which is used in the powered respiratory system. The advantage of splitting off the fluid from the supplying system of the powered respiratory is that only one system is needed for tempering the ear cushion and to supply the powered respiratory system with clean and purified fluid.

In a further embodiment, the fluid supply comprises a control unit to control the temperature, the flowrate, the pressure and/or the movement of the fluid for tempering the ear cushion. With a control unit the wearer/user of the system is able to adjust the tempering of the ear cushion more precisely and appropriate to user's needs. Controlling the fluid inside the system allows an even tempering of the ear cushion. This has the effect that the wearing/using of the ear cushion is more pleasant for the wearer and increases the wearing compliance of wearing/using the system.

The present disclosure further relates to a headset comprising the system according to the present disclosure and optional with a headband. The implementation of the system into a headset has the advantage, that wearing/using of a headset will be more comfortable or more pleasant for the wearer/user. The headset with the system according to the present disclosure provides for an active tempering system, which has the advantage that a fluid flows through the ear cushions by an over pressure or negative pressure in an improved way. Such an active tempering system provides for affecting the volume flow of the fluid and to temper the fluid. This active tempering system has the advantage that the temperature of the ear cushions can be adapted to the environment conditions, for example, by using a heated or cooled fluid in the active tempering system. With tempering an ear cushion, it is possible to increase the comfort during wearing, because the wearer has a more pleasant feeling by using the ear cushions according to the present disclosure and with that also the wearing of a headset is more pleasant. The tempered ear cushion has the advantage that feeling unwell because of too cold and/or to warm ears by using ear cushions will be reduced or avoided and thus, the risk of wearers for being sick reduced.

The present invention further relates to an ear cushion for a headset. The ear cushion comprises at least one ventilation passage allowing a flow of a tempering fluid therethrough. The ear cushion further comprises at least one interface connectable to a fluid supply through a fluid guide device of a system such that a fluid flow between the ear cushion and the fluid supply is achievable. The ear cushion optionally comprises at least one opening. Such an ear cushion may be beneficial as the ear cushion may be retrofitted to an existing system or headset thereby enabling the system or headset to provide an active tempering as described above. The retrofitted system or headset exhibits the same advantages as described above and below for the system according to the present disclosure and for the headset according to the present disclosure.

The present disclosure further relates to a fluid guide device for a headset connectable to a fluid supply and connectable to an interface of an ear cushion of a headset such that a flow of a tempering fluid provided by the fluid supply is achievable. Such a fluid guide device may be beneficial as the fluid guide device may be retrofitted to an existing system or headset thereby enabling the system or headset to provide an active tempering as described above. The retrofitted system or headset exhibits the same advantages as described above and below for the system according to the present disclosure and for the headset according to the present disclosure.

In one embodiment, the fluid guide device is integrated into a headband. Here, the headband of a headset forms a fluid guide device inside the headband of a headset. Alternatively, the fluid guide device may be attached to a headband of the headset. An example for attaching or mounting the fluid guide device to the headband is to fix the fluid guide device by using fixing elements, preferably clips and/or wire straps. With both alternatives, the effect is that the fluid guide device is not in the way and does not disturb when using and wearing the headset in order to minimize the risk that the fluid guide device gets caught somewhere when using the headset.

In a further embodiment the headset comprises hearing protection and/or electronic components. Therefore, the present disclosure helps maximizing the wearing comfort of the headset by tempering the ear cushion. Thus, the wearer feels the using of the headset as pleasant, because the wearer can control the temperature under the ear cushion by turning off or on the fluid supply of the system and, more specifically, by controlling the temperature of the fluid in the system. For instance, in a hot environment it is possible to increase the flow rate of the fluid and/or to adjust a lower temperature of the fluid to have a pleasurable wearing feeling. In a cold environment, for example, it is possible to reduce the flow rate of the fluid and/or to adjust a higher temperature of the fluid to avoid cold ears during the use of the headset. Therefore, the system of the present disclosure helps maximizing the wearing comfort during use of the headset. Such an increased wearing comfort leads to an increased wearing compliance of such a headset. Headsets with a hearing protection are well known and suitable for using in environment with a higher noise level to project the wearer against this noise. The headset may further comprise electronic device comprising at least one loudspeaker, at least one microphone, at least one battery/accumulator, at least one signal transmitting device, at least one amplifier, at least one electronic control unit, at least one active noise cancelling unit or any combinations thereof, the use of all these electronic components are optionally. An example for using a headset with an integrated electronic device is the use for communication with other persons or/and electronic units like speech recognition software. The system according to the present disclosure helps to increase the acceptance to wear the headset for a longer time, because the wearing is more pleasant.

A typical application for a headset with hearing protection and with electronic components/devices is in a noisy environment where the wearer has to protect and/or has to communicate for example with other persons but taking off of the headset is not possible or should not be done.

Examples for signal transmitting devices are electronic units for transmitting signals from one device to another one, corresponding for such a transmitting are Bluetooth® (by Bluetooth SIG), radio transmission, GSM™ (by GSM Association) or other technologies.

The present disclosure further relates to a headgear comprising the system according to the present disclosure. There are different kinds of headgears, typical examples include protective headgears, headgears for wearing during sandblasting, headgears for wearing during welding, headgears for using in noisy, dirty, dusty areas or with other pollution loads in the environment. A use of the system is also applicable in helmets for using a motorcycle, a bicycle, a racing vehicle, a flying machine or in other applications where the wearing of a helmet is necessary or mandatory.

The effect of using the system according to the present disclosure is to increase the willingness of the wearer to use the helmet or headgear as described before because the wearing is more comfortable.

The invention was described in various embodiments above. It is understood by a person skilled in the art, that one, several or all of the above-mentioned embodiments can be combined with each other.

The invention will now be described in more detail with reference to the following Figures exemplifying particular embodiments of the invention:

DETAILED DESCRIPTION OF THE FIGURES

Figure 1:
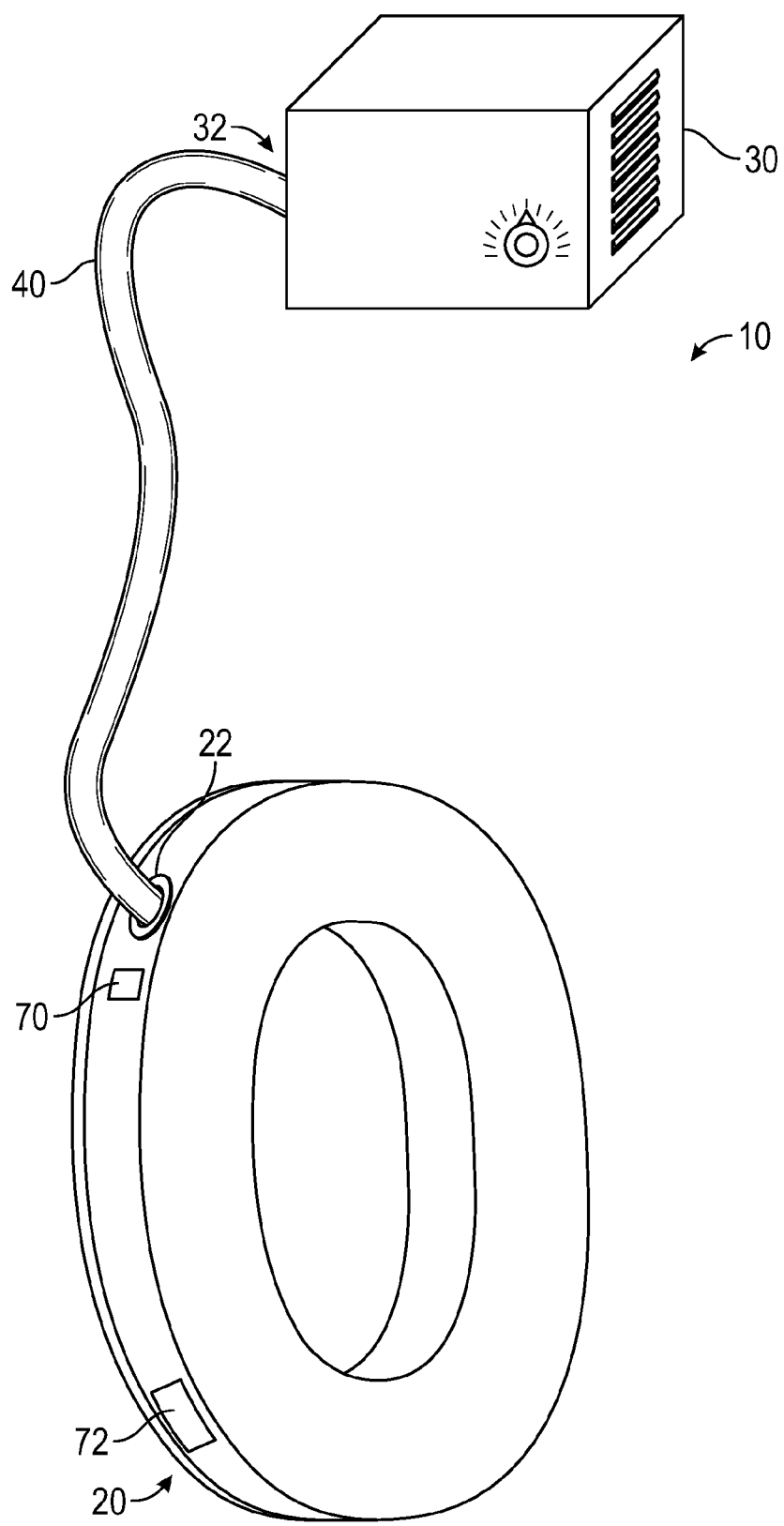
FIG. 1 is a perspective schematic view of a system according to one embodiment of the present disclosure.

FIG. 1 illustrates a system 10 according to one embodiment of the present disclosure. The system comprises an ear cushion 20 for a headset, a fluid supply 30 and a fluid guide device 40. The fluid guide device 40 is connected by a first interface 22 with the ear cushion 20 and a second interface 32 with the fluid supply 30, so that the ear cushion is in fluid communication with the fluid supply 30. The ear cushion 20 comprises a first opening 70 and a second opening 72. The first opening 70 has a smaller cross section than the second opening 72. The first opening 70 is positioned closer to the first interface 22. The function of the fluid guide device 40 is to guide a fluid from the fluid supply 30 to the ear cushion 20 and/or vice versa.

Figure 2:
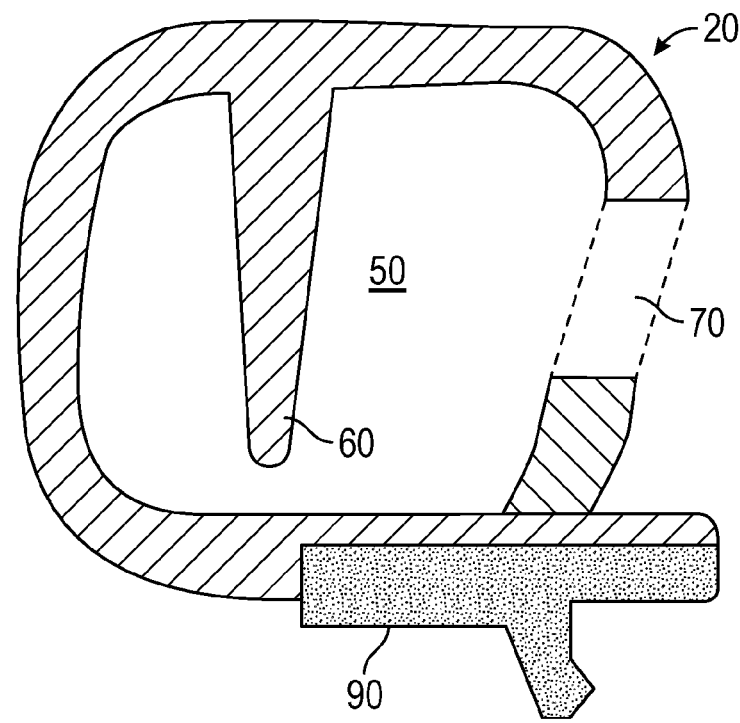
FIG. 2 is a cross-sectional view of the ear cushion according to the embodiment of the present disclosure of FIG. 1.

FIG. 2 illustrates a cross-sectional view of the ear cushion 20 of one embodiment of the present disclosure as shown in FIG. 1. Inside the ear cushion 20 is a ventilation passage 50 and an air deflector 60. The air deflector 60 is connected with the outer structure/contour of the ear cushion 20 and allows for modification of the fluid flow in the ventilation passage 50. In this embodiment the air deflector 60 extends into the ventilation passage 50 of the ear cushion 20. The first opening 70 is inside the external structure/contour of the ear cushion 20 and provides for a fluid intake or outlet through the opening 70 of the ventilation passage 50 inside the ear cushion 20. The function of a fixing element 90 is to mount the ear cushion 20 to the head, for example by form-locked fixing to the headset. A potential material for the fixing element 90 is plastic. A potential method to connect the fixing element 90 to the basic material of the ear cushion 20 is gluing.

Figure 3:
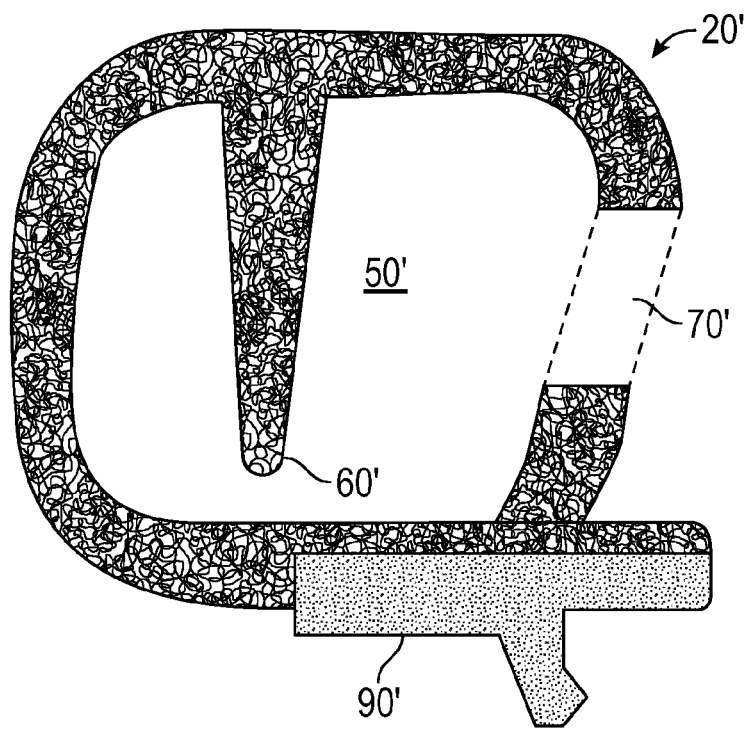
FIG. 3 is a cross-sectional view of the ear cushion according to a different embodiment of the present disclosure.

FIG. 3 illustrates a cross-sectional view of the ear cushion 20' similar to the embodiment of FIG. 1 of the present disclosure. FIG. 3 shows the same cross-sectional view as FIG. 2. The difference is that the basic material of the ear cushion 20' is a porous material. Inside the ear cushion 20' is a ventilation passage 50' and an air deflector 60'. The air deflector 60' is connected with the outer structure/contour of the ear cushion 20' for modification of the fluid flow in the ventilation passage 50'. In this embodiment the air deflector 60' extends into the ventilation passage 50' of the ear cushion 20'. The first opening 70' is inside the external structure/contour of the ear cushion 20' and provides for a fluid intake or outlet through the opening 70' of the ventilation passage 50' inside the ear cushion 20'. The function of a fixing element 90' is to mount the ear cushion 20' to the head, for example by form-locked fixing to the head set. A potential material for the fixing element 90' is plastic. A potential method to connect the fixing element 90' to the basic material of the ear cushion 20' is gluing.

Figure 4:
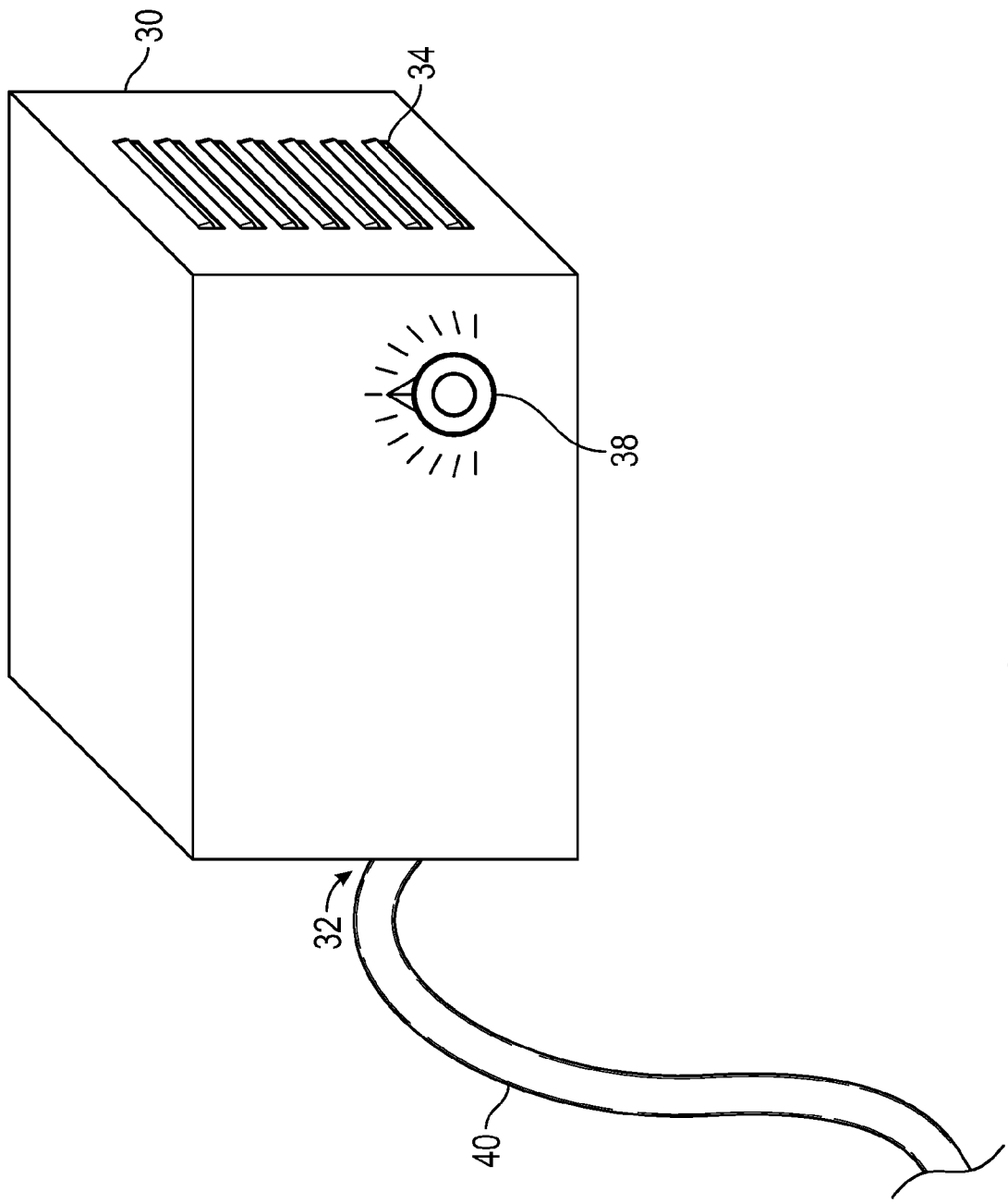
FIG. 4 is a perspective schematic view of a part of a system according to the embodiment of the invention of FIG. 1.

FIG. 4 illustrates a part of the system 10 (see FIG. 1) according to one embodiment of the present disclosure. The fluid supply 30 comprises ventilation slots 34 to allow a flow of a fluid out of the fluid supply 30 into the environment or into the counter direction. A control unit 38 is also optionally integrated into the fluid supply 30. Some parts inside the fluid supply 30 are not shown, for example a pressure changing device and/or a tempering device. The fluid supply 30 has the function to affect a fluid by overpressure or negative pressure, so that the ear cushion is in fluid communication with the fluid supply 30.

Figure 5:
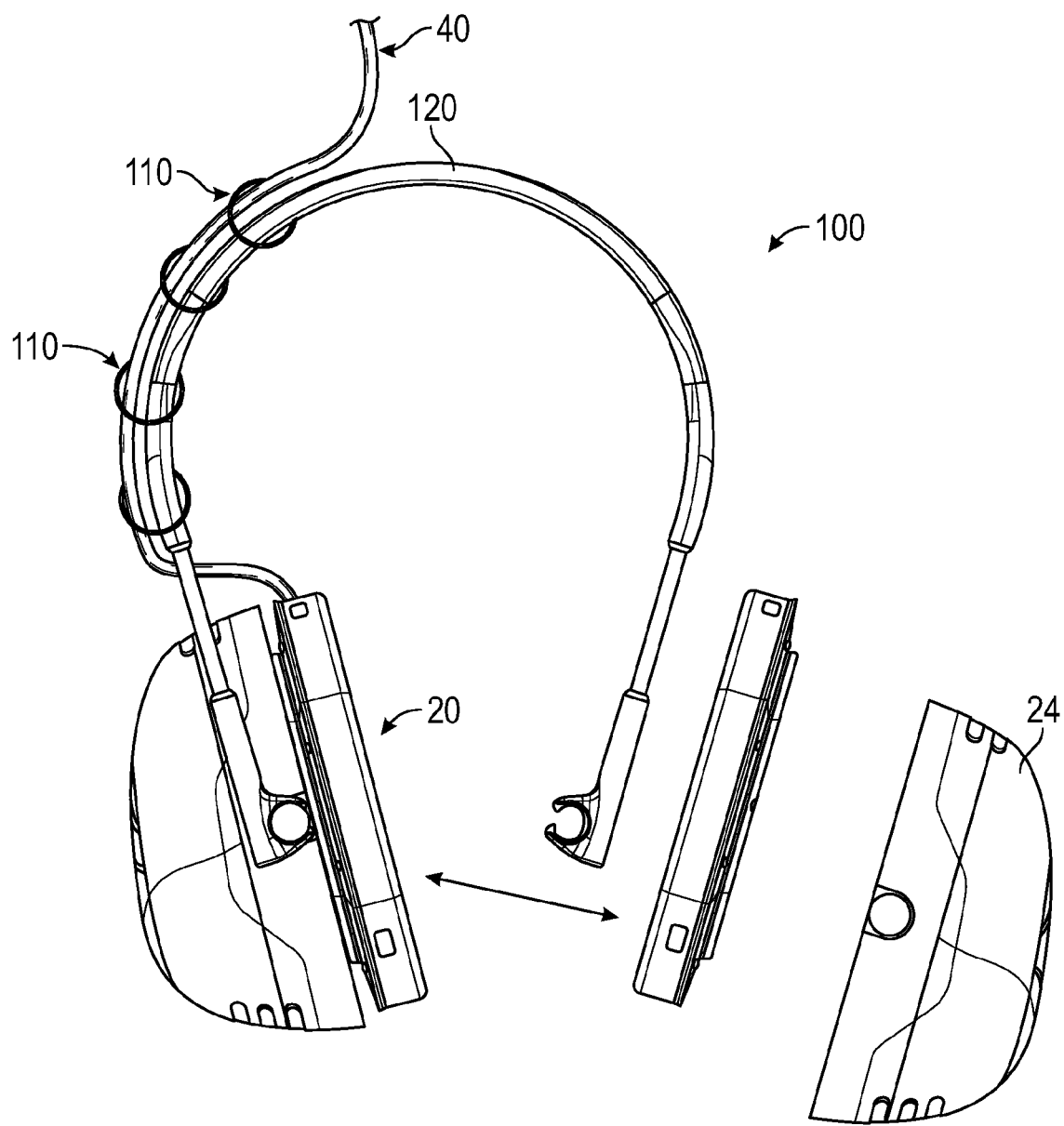
FIG. 5 is a perspective schematic view of a head set comprises parts of the system according to one embodiment of the present disclosure.

FIG. 5 illustrates a headset 100 according to one embodiment of the present disclosure. The headset 100 comprises ear cushions 20 and cups 24. On the left side of FIG. 5 the ear cushion 20 is connected to the cup 24 and the cup 24 is fixed to a headband 120. On the right side the ear cushion 20 and the cup 24 are shown in a not mounted position. The fluid guide device 40 is connected to the ear cushion 20 by the interface 22 (not shown in FIG. 5) and fixed by clips 110 to the headband 120 of the headset 100. The fixing of the fluid guide device 40 by clips 110 helps that the fluid guide device 40 is not in the way when using the headset 100. Only one fluid guide device is in so that the drawing remains clearly arranged.

Figure 6:
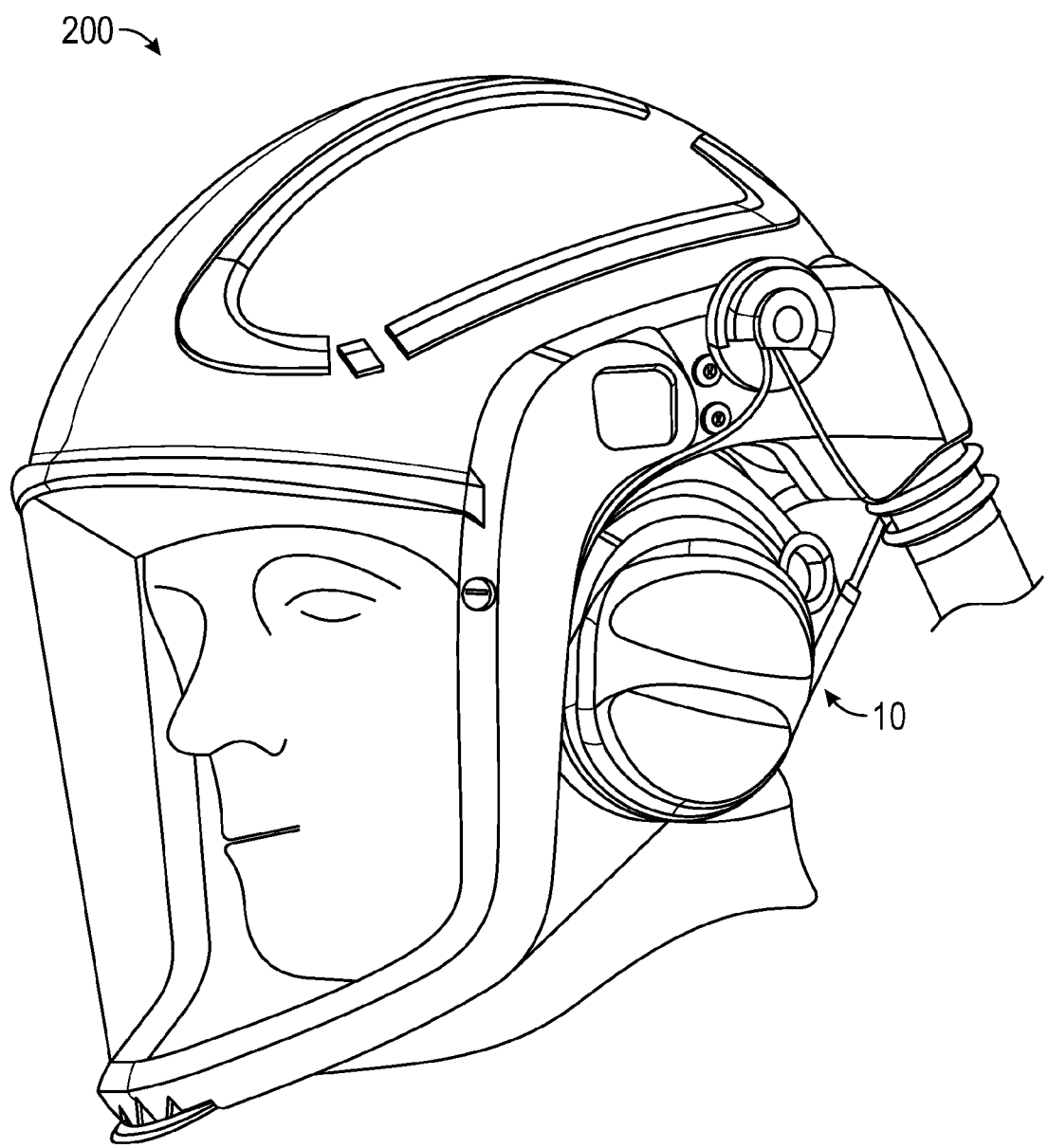
FIG. 6 is a perspective view of a user wearing a headgear comprises parts of the system according to an embodiment of the present disclosure.

FIG. 6 illustrates a headgear 200 according to one embodiment of the present disclosure. The system 10 of the present disclosure is integrated into the headgear 200.

The invention claimed is:

1. A system comprising at least one ear cushion for a headset and a fluid supply for supplying a fluid to the ear cushion, wherein the system comprises a fluid guide device that is connectable to the fluid supply and wherein the ear cushion comprises an interface for connecting the fluid guide device with the ear cushion, wherein the fluid supply is configured to provide heating or cooling fluid for adjusting the temperature of the ear cushion, wherein the fluid is air.

2. The system according to claim 1, wherein the ear cushion comprises a ventilation passage being in fluid communication with the interface.

3. The system according to claim 2, wherein the ventilation passage comprises at least one air deflector.

4. The system according to claim 2, wherein the ventilation passage comprises at least two openings with different cross sections of the openings, the two openings comprising an opening with a smaller cross section and an opening with a larger cross section.

5. The system according to claim 4, wherein the opening with the smaller cross section is positioned closer to the interface than the opening with the larger cross-section.

6. The system according to claim 1, wherein the fluid supply comprises a pressure change device to affect the pressure of the fluid and to allow a movement of the fluid from the fluid supply through the fluid guide device to the ear cushion or into the reverse direction.

7. The system according to claim 1, wherein the fluid supply and/or the fluid guide device comprises a tempering device for affecting the temperature of the fluid for tempering the ear cushion.

8. The system according to claim 1, wherein the fluid supply is a powered respirator.

9. The system according to claim 1, wherein the fluid supply comprises a control unit to control the temperature, the flowrate, the pressure and/or the movement of the fluid for tempering the ear cushion.

10. The system of claim 2, wherein the ear cushion comprises an opening.

11. The system of claim 6, wherein the pressure change device comprises a fan, a pump, a compressor, a pressure vessel, fluid pipeline or any combinations thereof.

12. An ear cushion for a headset, the ear cushion comprising a ventilation passage allowing a flow of a tempering fluid therethrough and further comprising an interface connectable to a fluid supply through a fluid guide device such that a fluid flow between the ear cushion and the fluid supply is achievable, the ear cushion comprises at least one opening, and wherein the fluid supply is configured to provide heating or cooling fluid for adjusting the temperature of the ear cushion.

13. A system comprising at least one ear cushion for a headset and a fluid supply for supplying a fluid to the ear cushion, wherein the system comprises a fluid guide device that is connectable to the fluid supply and wherein the ear cushion comprises an interface for connecting the fluid guide device with the ear cushion, wherein the fluid supply is configured to provide heating or cooling fluid for adjusting the temperature of the ear cushion, and wherein the ear cushion comprises at least one ventilation passage being in fluid communication with the interface.

14. The system according to claim 13, wherein the fluid supply comprises a pressure change device to affect the pressure of the fluid and to allow a movement of the fluid from the fluid supply through the fluid guide device to the ear cushion or into the reverse direction.

15. The system according to claim 14, wherein the fluid supply and/or the fluid guide device comprises a tempering device for affecting the temperature of the fluid for tempering the ear cushion.

16. The system according to claim 13, wherein the fluid comprises air.

17. The system according to claim 13, wherein the fluid supply is a powered respirator.

* * * * *